United States Patent [19]

Sarstedt

[11] Patent Number: 5,115,817
[45] Date of Patent: May 26, 1992

[54] BLOOD EXTRACTION DEVICE

[75] Inventor: Walter Sarstedt, Nümbrecht-Rommelsdorf, Fed. Rep. of Germany

[73] Assignee: Walter Sarstedt Geräte und Verbrauchsmaterial für Medizin und Wissenschaft, Nurmbrecht-Romelsdorf, Fed. Rep. of Germany; DEX

[21] Appl. No.: 675,638

[22] Filed: Mar. 26, 1991

[30] Foreign Application Priority Data

Nov. 17, 1990 [DE] Fed. Rep. of Germany ....... 4036673

[51] Int. Cl.$^5$ ................................................ A61B 5/00
[52] U.S. Cl. .................................................... 128/764
[58] Field of Search ............... 128/760, 763, 764, 770; 604/51, 52, 187, 264, 272

[56] References Cited

U.S. PATENT DOCUMENTS

| | | | |
|---|---|---|---|
| 3,500,821 | 3/1970 | Ogle | 128/764 |
| 3,648,684 | 3/1972 | Bamwell et al. | 128/764 |
| 3,814,079 | 6/1974 | LeRoy | 128/764 |
| 4,192,320 | 3/1980 | Megahed | 128/764 |

Primary Examiner—Max Hindenburg
Attorney, Agent, or Firm—Townsend and Townsend

[57] ABSTRACT

The object of the invention is a blood extraction device comprising a cannula (1) for insertion at its front end into the vein of a patient, the rear end (1') of the cannula opening in an inner tube (2) located in the interior of a sample tubule (3), which is closed hermetically at its rear end and closed at its front end except for an air bleeder (4). In the blood extraction position the inner tube (2) is secured against withdrawal out of the sample tubule (3) by means of a cap (5) having releasable axial locking means (6), preferably by means of a screw cap. A perforatable and self-closing membrane (7) is arranged in the front portion of the cap (5); this membrane sealingly closes the inner tube (2) at its front end (8) in the blood extraction position and simultaneously pushes the inner tube (2) without play against an abutment in the sample tubule (3). The inner tube (2) and the closure cap (5) are connected to each other by a tow-connection such that on axially removing the cap (5) from the sample tubule (3) the seal between the membrane (7) and the inner tube (2) is firstly cancelled and only thereafter the inner tube is driven therewith.

5 Claims, 1 Drawing Sheet

U.S. Patent
May 26, 1992
5,115,817
Fig. 1
Fig. 2
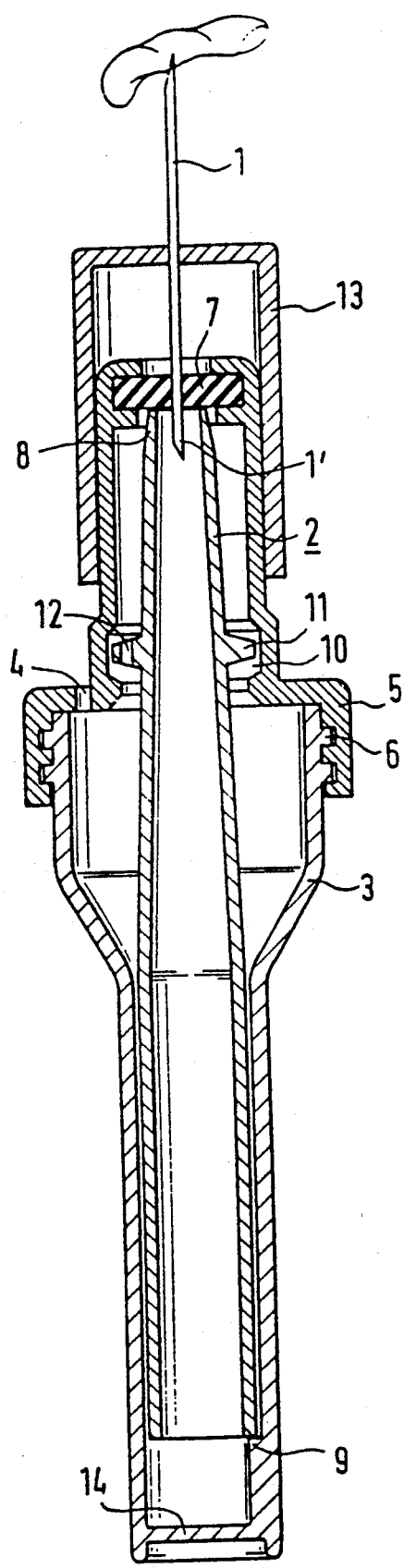
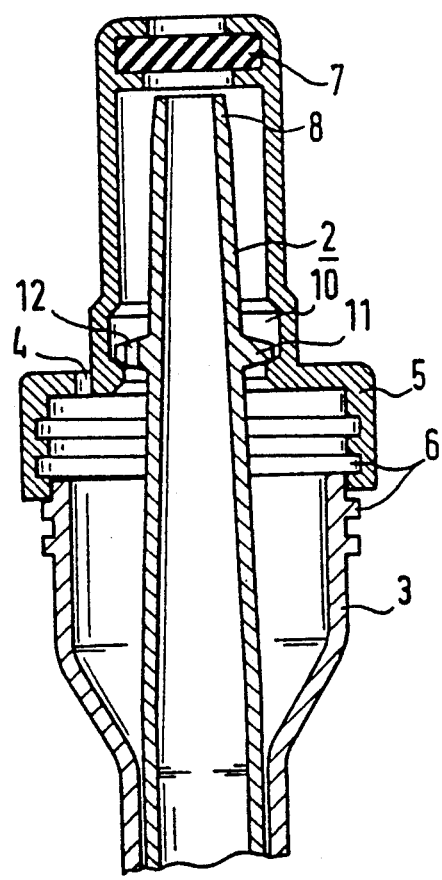

BLOOD EXTRACTION DEVICE

The invention relates to a blood extraction device of the kind set forth in the preamble of claim 1.

BACKGROUND OF THE INVENTION

A blood extraction device of this kind has already been proposed (DE-A-39 32 112), in which, after having pulled the cannula out of the vein, the blood present in the inner tube can flow out of the inner tube into the sample tubule, which can be assisted by a depression produced in the lower portion of the sample tubule on withdrawing the inner tube.

SUMMARY OF THE INVENTION

On the contrary, the invention relates to an improvement of the blood extraction device of this kind such that an axial relative displacement between the inner tube and the sample tubule is securely prevented when it is not desired, i.e. in particular during the extraction of blood, and that after the extraction of blood, the blood present in the inner tube is completely conveyed out therefrom into the sample tubule when the inner tube is withdrawn from the sample tubule.

In order to meet this object, provision is made for the features of the characterising portion of the claim.

In this manner, one is ensured that the inner tube is firmly connected to the sample tubule on extracting blood and is sealingly closed at the front by the self-closing membrane, such that during the extraction of blood an undesired relative displacement between the inner tube and the sample tubule is not possible.

Only when, after the extraction of blood, the axial locking means are released and the cap is axially removed, air can penetrate into the front end of the inner tube, such that during the withdrawal of the inner tube occuring because of the tow-connection, the blood contained in the inner tube is conveyed into the sample tubule.

BRIEF DESCRIPTION OF THE DRAWINGS

The invention will be thereafter described by way of example with reference to the drawings; the latter show:

FIG. 1 a partly cut out side view of a blood extraction device of the invention in the position of blood extraction, and FIG. 2 a section of the front portion of the device of the invention of figure 1 during the removal of the sealing cap from the sample tubule.

DESCRIPTION OF THE PREFERRED EMBODIMENTS

In figure 1, an inner tube 2 is located in an upwardly flaring sample tubule 3, which is hermetically closed at its rear end 14, in such a manner that an air passage still remains between the outer wall of the inner tube 2 and the inner wall of the sample tubule 3. In the position of blood extraction reproduced in FIG. 1, the rear end of the inner tube 2 reaches up to close to the rear end of the sample tubule 3 and rests there on an abutment 9 provided on the inner wall of the sample tubule 3 at a short distance from the end 14.

The front end of the sample tubule 3 is closed by a closure cap 5 which is screwed on the front end of the sample tubule 5 by means of a thread 6. In the closure cap 5 there is provided an opening 4 intended for venting the inner space of the sample tubule at the front end.

In the front part of the closure cap 5 is arranged a perforatable and self-closing membrane 7 which sealingly closes the front end 8 of the inner tube 2 in the blood extraction position of FIG. 1.

A ring-shaped recess 10 in the inner wall of the closure cap 5 accomodates a ring flange 11 having a vent opening 12 and provided on the inner tube 2.

A guide bushing 13 including a cannula 1 sharpened on both sides is engaged over the front part of the closure cap 5, and the front end of the cannula 1 is inserted into a vein only schematically indicated, while the rear end 1' has perforated the membrane 7 and reaches into the interior of the inner tube 2.

The described blood extraction device operates a follows:

In the blood extraction position of figure 1, blood flows via the cannula 1 into the interior of the inner tube 2. As soon as the desired filling extent is attained, the operator stops the extraction of blood, for which the sample tubule 3 is withdrawn from the guide bushing 13 jointly with the closure cap 5 firmly connected thereto; thereby the rear end 1' of the cannula 2 comes forwardly out of the membrane 7 and the latter automatically closes itself such that the front end 8 of the inner tube 2 is thereafter sealingly closed.

Thereafter, the closure cap 5 is unscrewed from the sample tubule and axially removed. During this, because of the play firstly present between the ring flange 11 and the rear boundary of the recess 10 (FIG. 1), the membrane 7 lifts away from the front end 8 of the inner tube 2, whereas the inner tube 2 is subsequently moved therewith by virtue of the tow-connection then provided for, after the play has been overcome.

By this, because of the venting of the front end 8 of the inner tube 2 provided via the venting bores 4, 12, the blood present in the inner tube 2 is conveyed at the bottom out of the inner tube 2 into the sample tubule 3. Thereby, the extracted blood is entirely contained in the sample tubule 3 after complete withdrawal of the inner tube 2.

I claim:

1. A blood extraction device comprising a cannula having a front end for insertion into the vein of a patient and a rear end;

a sample tubule having a front end and a closed rear end;

an inner tube located on an interior of the sample tubule, a front end of the inner tube being open and the rear end of the cannula communicating with the inner tube;

a cap releasably secured to the sample tubule so that the cap can be removed in an axial direction relation to the sample tubule, the cap closing the front end of the tubule;

means defining a vent communicating the front end of the tubule with an exterior thereof;

a self-closing, perforatable membrane mounted to the cap;

coupling means connecting the inner tube to the cap permitting limited, relative movement between the cap and the inner tube in an axial direction;

engagement means defined by the sample tubule adjacent the rear end thereof adapted to engage the rear end of the inner tube, a spacing between the engagement means and the membrane being selected so that the membrane engages the open end of the inner tube and biases the rear end of the inner tube into engagement with the engagement means to thereby form a seal between the membrane and the open end of the inner tube;

whereby axial movement of the cap relation to the sample tubule away from the rear end of the sample tubule first breaks the seal established between the membrane and the open end of the inner tube and, thereafter, the coupling means causes the inner tube to move with the cap in an axial direction.

2. A blood extraction device according to claim 1 wherein the coupling means comprises a recess in the cap and a ring flange defined by the inner tube adapted to loosely fit within the recess so as to permit limited, relative axial movement between the insert and the ring face and therewith between the cap and the inner tube.

3. A blood extraction device according to claim 1 including a vent opening in the ring flange.

4. A blood extraction device according to claim 1 wherein the engagement means includes a shoulder on the sample tubule.

5. A blood extraction device according to claim 1 including a thread connection releasably securing the cap to the sample tubule.

* * * * *